United States Patent [19]

Vichkanova et al.

[11] 4,436,732
[45] Mar. 13, 1984

[54] MEDICATED COMPOUND FOR TREATING DISEASES INFECTED BY VIRUS OF THE HERPES GROUP

[76] Inventors: Serafima A. Vichkanova, ulitsa Moskovskaya, 1, kv. 192, Ljubertsy, Moskovskaya oblast; Ljudmila D. Shipulina, 28, kv. 240, poselok Razvilka, Moskovskaya oblast; Vladimir I. Glyzin, ulitsa Shipilovskaya, 29, korpus 2 kv. 255, Moscow; Alexandr I. Bankovsky, ulitsa Institutskaya, 4, kv. 6, p/o "Vilar", Moskovskaya oblast; Mikhail G. Pimenov, Vtoraya Kvesisskaya, 24, korpus 2, kv. 8, Moscow; Klim I. Boryaev, ploschad Lenina, 5a, kv. 33, Chimkent, all of U.S.S.R.

[21] Appl. No.: 315,016

[22] Filed: Oct. 26, 1981

[51] Int. Cl.³ .................. A61k 31/70; C13K 11/00
[52] U.S. Cl. ................................ 424/180; 536/1.1
[58] Field of Search .............. 424/180; 536/1, 1.1

[56] References Cited

PUBLICATIONS

Chem. Abs. 87: 79461, Ghosal et al., Phytopathology 1977 67(4), pp. 548–550, (Eng).
Chem. Abs. 95: 162139r, Lambiv et al., Probl. Vutr. Med., 1980, 8(2), pp. 109–155, (Bulg).
Chem. Abs. 91:83232, Shank aranrayan et al., Ind. J. Pharm. Sci. 1979, 41(2), 78–79, (Eng).

Primary Examiner—Donald B. Moyer
Assistant Examiner—Shawn P. Foley
Attorney, Agent, or Firm—Robert E. Burns; Emmanuel J. Lobato; Bruce L. Adams

[57] ABSTRACT

A pharmaceutical composition for the treatment of diseases caused by a virus pertaining to the herpes group comprising an active principle: 2-C-β-D-glucopyranosyl-1,3,6,7-tetraoxyxanthone of the formula:

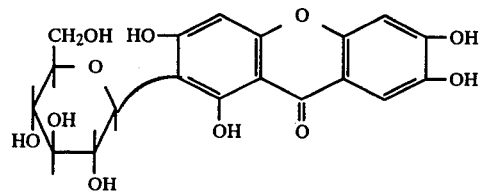

in combination with a pharmaceutical vehicle.

3 Claims, No Drawings

MEDICATED COMPOUND FOR TREATING DISEASES INFECTED BY VIRUS OF THE HERPES GROUP

FIELD OF THE INVENTION

The present invention relates to pharmaceutical compositions for treating diseases caused by a virus of the herpes group (HV).

BACKGROUND OF THE INVENTION

Virus infections are widespread among the world population. Among most widespread and dangerous virus infections there are diseases caused by viruses of the herpes group including zoster, herpetic keratitises, keratoconjunctivitises, virus hepatitises; encephalitises and the like. Prominent characteristics of the herpetic infection substantially hindering the control thereof reside in a long-time persistance of the herpes virus in the organism, frequent recurrences and plurality of clinical signs.

Common herpes (Herpes simplex) is characterized mainly by vesicular eruption. The infection intensity is different and can be accompanied by either moderate general symptoms of herpetic fever with a high body temperature, depression, headache and pain in joints. The signs of the disease can be also stomatitis, glossitis, keratitis and keratoconjunctivitis, pharyngitis, vesicular eruption on mucous membranes and skin. More frequently injured is the face in the regions of mouth, nose, eyelid, as well as genitalia. In the case of Herpes zoster the dermal injuries are preceded by inflammation phenomena and changes in ganglia roots and posterior columns of the spinal cord which is accompanied by strong, often intolerable pains along the nerve and local dermal signs: edema, itching, vesicular eruption. In herpetic diseases there are rather frequent cases of herpetic hepatitis in both children and adults. Relatively insufficiently studied are disturbances of the central nervous system in the form of meningitis, encephalitis and encephalomielitis. A generalized form of herpes with lethal outcome.

Despite an extensive search for preparations with antivirus activity, the problem of investigation of viral diseases caused by a virus of the herpes group still remains urgent. The existing antivirus preparations do not satisfy all the requirements imposed thereon and their application does not result in a full recovery, nor prevention from recurrences.

For the treatment of herpetic diseases attempts have been made to use antibiotics, certain chemical compositions, corticoids, specific and non-specific vaccinotherapy. It has been found out that the use of sulphanylamides and antibiotics does not provide any effect on the course of the herpetic disease and can merely prevent or eliminate the bacterial infection. Chemical preparations employed for the treatment of these diseases, namely: analogues of pyrimidine bases, JDU (5-iodine-2-desoxyuridine), 5-fluorouracyl are antimetabolites and, exerting an effect on the virus, they also affect the organism. Furthermore, they are rather toxic substances.

Consequently, the known antiviral preparations do not satisfy all necessary requirements (do not prevent recurrences, do not cause full recovery); thus, the problem of treating virus diseases caused by a virus pertaining to the group of herpes still has to be solved.

SUMMARY OF THE INVENTION

It is an object of the present invention to provide a composition for treating diseases caused by a virus of the herpes group which possesses a high selective activity relative to the infectant, ensures a high therapeutic effect, is non-toxic and available in manufacture.

These and other objects of the present invention are accomplished by a composition which comprises an active principle, namely: 2-C-$\beta$-D-glucopyranosyl-1,3,6,7-tetraoxyxanthone of the general formula:

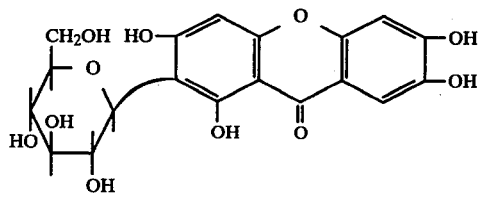

in combination with a pharmaceutical filler.

The active principle is an individual substance of the xanthone nature (mangiferin euxantogen) of the formula $C_{19}H_{18}O_{11}$. As to its appearance, it is a yellow crystalline substance with a melting point of 258°–261° C., sparingly soluble in ethanol, insoluble in water, chloroform, ethyl ether. This compound has not been hitherto used in the medicine.

As has been mentioned hereinbefore, the active principle is used in combination with pharmaceutical fillers.

In the case of viral diseases of skin and mucous membranes (Herpes simplex, Herpes zoster, lichen planus, herpes genitalis, aphthous stomatitis, pharyngitises, rhinitises and other diseases of the viral ethiology), for external application, it is advisable to make use of a composition containing said active principle in a combination with a pharmaceutical vehicle suitable for ointments comprising a mixture of vaseline oil and vaseline.

It is advisable to use a composition containing the following proportions of components: 2 to 5% by weight of the active principle, 4 to 10% of vaseline oil and 85 to 96% by weight of vaseline.

For per os administration it is preferable to use the medicated preparation in the form of tablets. To this end, as the pharmaceutical vehicle use is made of milk sugar, starch talc and calcium stearate. It is advisable to use tablets of the following composition: 40% by weight of the active principle, 40% by weight of milk sugar, 17% by weight of starch, 2% by weight of talc and 1% by weight of calcium stearate. This preparation can be administered in the case of the above-mentioned diseases, as well as in the case of viral hepatitis, encephalitis, meningitis and the like.

DETAILED DESCRIPTION OF THE INVENTION

The preparation according to the present invention has been named ALPIZARIN.

The study of antiviral properties of the active principle has been carried out in in vitro experiments in a culture of cells of fibroblasts of a chicken embryo following a commonly employed procedure for primary screening of antiviral preparations. Cells are grown in flasks or test-tubes on the nutrient medium 199 with the addition of 5 to 10 vol.% of cattle serum. Then, for the contact of the virus with cells, into the flasks a virus-containing material is added in doses of 1, 10, 100 and 1,000 $TCD_{50}$. Adsorption of the virus on cells is effected at room temperature for one hour, whereafter the medium containing the virus is removed and the nutrient medium 199 is introduced into the flasks or test-tubes; the medium contains the active principle in a maximum tolerable concentration for cells (the substance in this concentration does not possess the cytotoxic effect). Flasks or test-tubes are then subjected to thermosetting at the temperature of 37° C. The virus-suppressing effect is determined for 5 days by way of comparison of the presence of cytopathogenic effect in the control and test flasks and test-tubes. As the control use is made of: control of the single layer of cells, the control of the active principle without virus and the control of the virus without the active principle.

As a result, it has been found that the active principle in the concentration of 10 μg/ml possesses a high virus-suppressing effect in respect of 100 $TCD_{50}$ HV.

The chemotherapeutic effect of the active principle and the pharmaceutical composition on the whole has been studied on an experimental virus model of herpetic encephalitis of white mice. In the experiments more than 1,500 animals were used. To obtain the experimental encephalitis, white mice weighing 8–10 g have been infected intracerebrally. Prior to the infection the animal head skin is smeared with iodine, then ten-times dilutions of the virus-containing liquid in the volume of 0.03 ml are injected by means of a tuberculin syringe into the supraorbital area near the front median line to a depth of 1–2 mm directly into the brain. 3 to 7 days thereafter in the animals there were observed the disease signs (excitation, coordination disturbance, adynamia, paresis and paralysis) which were rapidly intensified and terminated in death. The experiments were assessed by the animal survival (in percent) and by the average life span of the test animals as compared to the control.

For treatment purposes the active principle or the medicated compound in the form of tablets is administered to the infected animals per os by means of a gastric tube as an aqueous suspension in the volume of 0.5 ml in doses of 20 to 500 mg/kg of the body weight 1 or 2 times per day. The tests have been carried out according to three schemes. In the first scheme, in order to preliminarily saturate the animal's organism with the active principle or the preparation were administered to the animals 1–2 days before the infection (preventive test). In the second scheme, to reveal the therapeutic effect of the active principle or the pharmaceutical composition, the compositions were introduced on the infection day and one or two days after the infection. In the third scheme (treatment-prophylaxis) the active principle or the medicated compound is administered the day before the infection or on the infection day, in both cases the treatment of the animal is continued for 5 to 7 days after the infection.

Upon the administration of the active principle or the pharmaceutical composition according to the first two schemes the death of the animals occurred substantially within the same time limits, as in the control animals, therefore it was impossible to reveal statistically certain chemotherapeutic effect of the medicated compound or the active principle.

The most advantageous chemotherapeutic effect of the active principle or the pharmaceutical composition is manifested under the conditions of the treatment-prophylaxis application (third scheme). The test results are shown in the following Tables 1 and 2.

TABLE 1

| Number of administrations | Dose, mg/mice | Survival, % | Life span, days | P |
|---|---|---|---|---|
| once a day | 5 | 70 | 13.1 ± 2.7 | above 0.5 |
|  | 1 | 90 | 14.0 ± 2.2 | above 0.25 |
|  | 0.2 | 90 | 14.0 ± 2.3 | above 0.25 |
|  | 0.04 | 80 | 13.3 ± 2.5 | above 0.5 |
| Two times a day | 5 | 90 | 14.3 ± 2.5 | above 0.1 |
|  | 1 | 100 | 15.0 ± | below 0.05 |
|  | 0.2 | 100 | 15.0 ± | below 0.05 |
|  | 0.04 | 90 | 14.1 ± 0.9 | above 0.1 |
| Control |  | 70 | 12.7 ± 2.6 |  |

From the data shown in Table 1 it is seen that upon administration of the active principle or the pharmaceutical composition the highest, statistically certain chemotherapeutic effect is attained upon its administration two times a day.

TABLE 2

| Moment of administration of the preparation | Dose of the preparation, mg/mice | Average life span, days | P |
|---|---|---|---|
| one day before infection | 5 | 6.13 ± 1.04 | below 0.05 |
|  | 2 | 6.05 ± 0.83 | below 0.05 |
|  | 1 | 5.6 ± 0.82 | 0.05 |
| on the infection day | 5 | 6.41 ± 0.71 | below 0.05 |
|  | 2 | 5.0 ± 0.56 | above 0.5 |
|  | 1 | 5.16 ± 0.91 | above 0.25 |
| Control |  | 4.78 ± 0.46 |  |

From Table 2 it follows that the chemotherapeutic effect of the active principle or the pharmaceutical composition is the highest upon their administration in maximum shortest time of the infection.

The study of pharmacological properties of the active principle is carried out in two ways: the effect on the cardio-vascular, central nervous systems; cardiorhythmic effect; on the system of blood coagulation, anti-inflammation and anti-ulcer and antidiabetic effect.

The study of the effect of this compound on the characteristics of hemodynamics and breathing has been carried out in an acute experiment on 6 narcotized cats (urethane 1.0 g/kg, chloralose 60 mg/kg) upon the intra-stomach administration of the active principle in the dose of 50 mg/kg. In each cat simultaneously recorded were the breathing frequency cardiac contraction frequency, systemic arterial pressure, amplitude of the volume blood flow in the abdominal aorta, amplitude of the brain rheograms and femur muscles rheorgrams.

The test results have shown that the active principle slightly lowers the systemic arterial pressure. The other characteristics of hemodynamics are not substantially changed. It has been found that the breathing frequency is reduced by 21% (10 minutes, P below 0.05) and by 32% (30 minutes, P below 0.01). The values of reduction of the arterial pressure and breathing frequency 60 and 90 minutes after the administration of this compound do not differ from the control.

The cardiological effect of the active principle has been studied in experiments on an isolated cat's heart; the effect on electrocardiographic characteristics has been studied in experiments on rabbits; the vasodilative effect—on vessels of an isolated rabbit's ear; the spasmolytic effect—on acetylcholine and barium spasms of smooth muscles of an isolated section of a rat's small intestine.

The studies have shown that upon the intravenous administration to rabbits of the active principle in the dose of 20 mg/kg it causes increased amplitude of cardiac contractions by 34% (P=0.05), in the dose of 50 mg/kg—by 41% (P=0.05); rarefaction of the rhythm of cardiac contractions in rabbits by 10-18% on the average and increase of the voltage of the peak P by 32%. Upon the intra-stomach administration in doses of 50 and 150 mg/kg the active principle provides no substantial effect on the rhythm of cardiac contractions and the duration of intervals of the cardiac cycle. A slight increase of the voltage of the peak P on the average by 20% is observed. Therefore, the active principle possesses no vasodilative and spasmolytic effect; a slight cardiostimulant effect of the active principle has no practical significance.

The cardiorhythmic effect of the active principle has been studied on the rat's aconitine model of arrhythmia upon its intravenous administration in the doses of 10 and 50 mg/kg. Analysis of the electrocardiograms has shown that the active principle in the studied doses possesses no cardiorhythmic effect.

The neurotropic activity of the active principle is assessed through its influence upon the somnific effects of hexenal or chloralhydrate. The substance is introduced per os in the doses of 1, 10 and 100 mg/kg. In these doses the compound provides no substantial effect on the duration of the sleep caused by chloralhydrate or hexenal.

The anti-ulcerous effect of the active principle has been studied on the model of caffeine-arsenic ulcer in rats. The substance is administered per os for nine days in the doses of 1, 10 and 20 mg/kg. It has been found that the compound provides a weak anti-ulcerous effect in the dose of 20 mg/kg.

In acute tests on cats the effect of the active principle on the intensity of bile secretion has been studied. In doses of 20 and 50 mg/kg the compound does not increase the bile secretion intensity.

The effect of the active principle on the acute exudative and chronical proliferative phases of inflammation in doses of 10 and 50 mg/kg has been studied upon per os administration to mice. The investigation results have shown that the compound has but a slight antiphlogistic effect: in the dose of 50 mg/kg it suppresses the development of the exudative phase of inflammation; possesses an antiphlogistic activity relative to formalin 12.7 (P below 0.005) and dextran 16.5 (P below 0.05) edema, lowers penetration of skin vessels by 15% (P below 0.05); on a model of a chronical proliferative inflammation it somewhat suppresses the exudative phase and retards the formation of a granulation-fibrous tissue during the proliferative stage of the chronical inflammation.

The study of the effect of the active principle on certain characteristics of blood coagulation has been carried out on 5 rabbits. The compound is administered per os in the dose of 50 mg/kg as a suspension in a 2% starch paste. Blood has been examined prior to the administration and during 4 hours after a single-time administration of the suspension; determined are: blood plasma recalcification, thrombin time, thrombelastographic characteristics and thrombocyte concentration. The analysis of the obtained results show that the active principle in the studied dose does not substantially affect the blood coagulation process.

To reveal the antidiabetic effect of the active principle, its effect on the content of glucose in rabbit's blood under the conditions of alimentary carbohydrate load has been studied. The active principle is administered in doses of 50 and 100 mg/kg once per os through a tube in a 1% starch paste. The experiment scheme is the following: the content of glucose in blood is determined in rabbit's blood on an empty stomach, and 40 minutes thereafter the content of glucose is again determined in blood. Afterwards, glucose is administered to the rabbits at the rate of 1.5 g/kg and the content of glucose in blood is determined 15, 30, 45, 60, 90 and 120 minutes after the administration thereof. The results thus obtained have demonstrated that the active principle in the dose of 50 mg/kg provides no effect of the character of variation of the glycemic curve under the conditions of carbohydrate load; in the dose of 100 mg/kg the glucose tolerance of rabbits is uncertainly increased by 14%.

Therefore, the investigations of pharmacological properties of the active principle have not revealed its essential activity in the above-described aspects.

The study of an acute toxicity and tolerance of the active principle and the medicated compound in the form of tablets has been carried out on white mice, rats, guinea pigs and dogs with different modes of administration.

The active principle and tablets of the are administered in the form of an aqueous suspension hypodermally, intraperitoneally and in stomach. It has been found that in the case of the intraperitoneal administration of the active principle and the pharmaceutical composition $LD_{50}$ is 3,000 to 4,000 mg/kg; in the case of hypodermal administration—above 5,000 mg/kg, and in the case of in-stomach administration—10,000 mg/kg.

The pharmaceutical composition according to the present invention in the form of an ointment also features a good tolerance and possesses no irritating effect on the skin. Thus, upon the application of a 10% ointment for 2 months on the skin of white rats, 1% ointment for 10 days on an eye mucous membrane of rabbits and 10% ointment on the vagina mucous membrane of white rats for 1.5 months no phenomena of the irritation effect on the site of application have been observed and no pathomorphological changes of the inner organs have been revealed.

The study of the teratogenic activity of the active principle has been carried out on 15 couples of adult rats weighing 350 g divided into 3 groups of 5 couples in each. The females of the first group were daily administred 10 mg/kg of the active principle per os for 30 days until the birth of small rats; the females of the second group were administered 100 mg/kg of the active principle during the same period; the females of the third group were the control.

It has been found that the active principles possesses no teratogenic properties: the small rats of the test groups were born in time, as compared to the control group, they were in adequate numbers and healthy.

The active principle possesses no mutagenous activity.

Therefore, both the active principle and the medicated compound based thereon are low-toxic.

The ointment forms of the medicated compound have been studied in dermatological, stomatological and otolaryngological clinics. The study has been carried out on 981 patients. Use was made of ointments containing 1% by weight, 2% by weight, 5% by weight and 10% by weight of the active principle. The ointments were administered by rubbing-in or application 1 to 3 times a day. The data of clinical studies are shown in Table 3 hereinbelow.

TABLE 3

| Kind of disease | Number of patients | | Conclusion |
|---|---|---|---|
| | Positive effect | Negative effect | |
| 1. Dermatology | | | The highest efficiency is noted for lichen pemphigoides of different localization, lichen planus, flat warts, acute aphthous stomatitis, chronical recurring stomatitis, viral diseases of otolaryngological organs. The preparation is substantially non-toxic. |
| Herpes simplex, acute and chronical, recurring of different localization | 180 | 12 | |
| Herpes zoster | 23 | 12 | |
| lichen planus | 18 | 3 | |
| warts (flat and common) | 65 | 17 | |
| psoriasis | 37 | 59 | |
| other viral diseases including neorodermite, eczema, dermatitis, pointed condyloma and the like | 221 | 51 | |
| 2. Stomatology | | | |
| acute aphthous stomatitis | 30 | 10 | |
| chronical recurring aphthous stomatitis | 30 | 10 | |
| proliferative exudative erythema | 23 | 22 | |
| acute and chronical recurring herpes of oral cavity | 70 | 5 | |
| 3. Otolaryngology | | | |
| otitis | 10 | 0 | |
| laryngitis and rhinitis of viral etiology | 65 | 0 | |
| TOTAL | 780 | 201 | |

In the case of treatment of Herpes simplex on the second day the edematic character and intensity of vesiculae were lowered, on the 3-d day a thin crust was formed in the central part of vesiculae, eruption of new elements stopped and recovery was observed on the 5–7-th day.

A positive therapeutic effect is noted in children suffering from flat warts. Eruption was fully removed with 7–10 days. After the removal of the eruption of molluscum contagiosum the children were administered a 2% ointment to prevent from recurrence of the disease and complications due to pyococcus infection which gave a positive therapeutic effect.

In the case of lichen planum the therapeutic efficiency of ointments resides in the following: within the first day itching phenomena disappeared in the patients and a partial regress occurred within the following days. No new eruption is observed during the treatment with the ointments. However, no full resolution of papulous eruption was noted. For this reason, together with the administration of ointments, prednisolone was prescribed per os in the dose of 15 mg per day with a subsequent reduction of the dose thereof and cancellation after 21–25 days which enabled a full clinical recovery.

In the case of psoriasis, neuridermite, common warts and some other diseases the effect of ointment forms is manifested less clearly.

Therefore, in dermatology the highest efficiency is noted for Herpes simplex of various localization, lichen planum and flat warts.

In stomatology, ointment forms were used by application of 1 to 4 times a day in the case of acute and chronic stomatitis, multi-form erythema, herpes and other diseases. The efficiency of ointment forms containing 2% by weight and 5% by weight of the active principle is noted in the case of: herpes of lips—resolution of the process was observed within 5 to 7 days (usually 10–14 days), acute aphthous stomatitis—epithelization of erosions was observed within 3–5 days (general progress—up to 7–14 days).

In patients suffering from multi-form exudative erythema and chronic recurring aphthous stomatitis the employed ointment forms manifested a weaker effect.

In otolaryngology, ointment forms were employed in the case of acute respiratory diseases, acute bullous otitis, exacerbation of vasomotor rhinitis with herpetic eruption on the lip skin, nose and in acute external otitis.

In the case of acute respiratory diseases a high efficiency of ointment forms is observed; the use of ointments within the first two days substantially fully stops the development of the disease. In the case of herpetic eruption and bullous otitis the administration of ointment forms accelerated the process extinction by 2–3 days on the average and upon early administration it fully prevented the development of vesicular elements.

A good therapeutic effect in the case of all the above-mentioned diseases is attained through the use of ointment forms containing 2 to 5% by weight of the active principle. Increasing the active principle content up to 10% does not cause an enhanced therapeutic effect. Decreasing the content of the active principle to 1% slightly lowers the therapeutic effect of such ointment.

The preparation should be preferably administered as a 2% and 5% ointment 3–3 times a day at a single dose of from 0.2–1.0 g on the average depending on the character of the disease. Thus, treatment of viral skin diseases is effected by lubricating, rubbing-in or application with 2% or 5% ointment 1 to 3 times a day. The preparation is deposited by way of lubrication, application or by means of turundae 1–3 times a day. In the treatment of rhinitises of the viral etiology, it is advisable to smear the nose mucous membrane with a 2% ointment 1 to 3 times a day. In the treatment of otisises of the viral etiology it is advisable to introduce a 2% ointment by means of turundae 1–3 times a day. In the case of viral diseases of genitalia and anus, it is advisable to carry out treatment by smearing with a 2–5% ointment 1 to 3 times a day.

The duration of the treatment course is determined in each particular case depending on the type of the disease and individual tolerance of the preparation (i.e. from several days to 3 months).

In the case of a chronic recurring progress of the disease, it is possible to use repeated courses of treatment following the above-described scheme.

It is advisable to use 10 to 50 g of an ointment per patient for one treatment course.

Thus, in the case of Herpes simplex of lips, nose wings, viral otitis and rhinitis, it is sufficient to use 10 g of a 2% ointment for the treatment course; in the case of viral stomatitis and herpes genitalis—10–20 g of a 2–5% ointment; in the case of more extensive skin injuries, for example Herpes zoster—20 to 50 g of a 5% ointment.

The medicated compound according to the present invention widens the therapeutic opportunities of preparations of similar effect. It has no side phenomena and can be used both under stationary and ambulatory conditions.

No contraindications to the administration of the preparation have been found.

The preparation according to the present invention should be stored in a cool, light-protected place.

The active principle—2-c-β-D-glucopyranosyl-1,3,6,7-tetraoxyxanthone (mangiferin) can be prepared from the herb of *Hedysarum alpinum, Hedysarum flavescenes* sp. Fabaceae).

The over-ground part of the herb is extracted with a 80% ethanol at a temperature of from 60° to 70° C. for 4 hours. The volume ratio between the vegetable material and the extraction agent is equal to 1:10 respectively. Extraction is effected for 4 times. The combined extracts are evaporated, then combined with hot water (90°–95° C.) and the resulting mixture is settled for 12–14 hours at a temperature of from 5° to 10° C. The residue (accompanying products) is filtered-off and the mangiferin-containing solution is purified with chloroform. The purified solution is repeatedly treated with butanol saturated with water. Butanol extracts are evaporated in vacuum, cooled at a temperature of from 5° to 10° C. for 14 to 16 hours and the precipitate is filtered-off, then recrystallized from a mixture of dioxane-water (1:1). The pharmaceutical composition according to the present invention in the form of an ointment can have, for example, the following preferable compositions:

|  | Composition I |  |
|---|---|---|
| active principle (mangiferin) | 2 g |
| vaseline oil | 4 g |
| vaseline | to 100 g |
|  | Composition II |  |
| active principle (mangiferin) | 5 g |
| vaseline oil | 10 g |
| vaseline | to 100 g. |

Ointments of the above-mentioned compositions can be prepared in the following manner.

Mangiferin is disintegrated into a fine powder by thoroughly rubbing it in a porcelain mortar. To the resulting powder the required amount of vaseline oil is added and again the whole mass is rubbed. Thereafter, vaseline is added in several portions under continuous stirring.

The medicated compound in the tablet form may have the following composition:

| active principle (mangiferin) | 0.1 g |
|---|---|
| milk sugar | 0.1 g |
| starch | 0.0425 g |
| talc | 0.005 g |
| calcium stearate | 0.0025 g |
| total weight of a tablet | 0.25 g |

The tabletted medicated compound of the above-given composition can be prepared in the following manner.

All the components of the tablet mass are preliminarily screened. Then powders of mangiferin, milk sugar and starch are intermixed. The resulting mixture is thoroughly agitated and combined with a 5% starch paste. Then the resulting mass is rubbed through a sieve with a mesh size of 1.5–2 mm. The resulting granulate is dried at room temperature for one day. The resulting granules are powdered with pre-dried starch, talc and calcium stearate and again rubbed through a sieve, whereafter they are tabletted.

What is claimed is:

1. A method of treating a herpes viral infection which comprises administering to a patient suffering from said infection a pharmaceutical composition containing as an active ingredient 2-C-β-D-glucopyranosyl-1,3,6,7-tetraoxyxanthone of the formula:

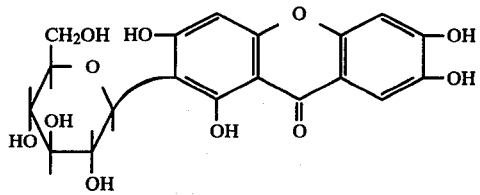

in an antiviral effective amount.

2. The method of claim 1 in which said pharmaceutical composition is in the form of an ointment and is administered externally.

3. The method of claim 1 in which said pharmaceutical composition is in the form of a tablet and is administered orally.

* * * * *